United States Patent [19]

Upsher

[11] Patent Number: 5,178,131
[45] Date of Patent: Jan. 12, 1993

[54] WATERPROOFED LARYNGOSCOPE HANDLE

[75] Inventor: Michael Upsher, San Mateo, Calif.
[73] Assignee: Upsher Laryngoscope Corporation, Foster City, Calif.
[21] Appl. No.: 693,804
[22] Filed: Apr. 30, 1991
[51] Int. Cl.$^5$ ............................................. A61B 1/06
[52] U.S. Cl. ........................................ 128/11; 128/6
[58] Field of Search .................. 128/4, 6, 9, 10, 11

[56] References Cited

U.S. PATENT DOCUMENTS

| | | | |
|---|---|---|---|
| 3,766,909 | 10/1973 | Ozbey | 128/11 |
| 3,826,248 | 7/1974 | Gobels | 128/11 |
| 3,913,568 | 10/1975 | Carpenter | 128/11 |
| 4,406,280 | 9/1983 | Upsher | 128/11 |
| 4,437,458 | 3/1984 | Upsher | 128/11 |
| 4,517,964 | 5/1985 | Upsher | 128/11 |
| 4,561,446 | 12/1985 | Hetz | 128/7 |
| 4,592,343 | 6/1986 | Upsher | 128/11 |
| 4,669,449 | 6/1987 | Bauman | 128/11 |
| 4,679,547 | 7/1987 | Bauman | 128/10 |
| 4,694,822 | 9/1987 | Bauman | 128/11 |
| 4,722,000 | 1/1988 | Chatenever | 128/6 |
| 4,729,367 | 3/1988 | Bauman | 128/11 |
| 4,815,451 | 3/1989 | Bauman | 128/11 |
| 4,854,302 | 8/1989 | Allred, III | 128/6 |
| 4,884,558 | 12/1989 | Gorski et al. | 128/11 |

Primary Examiner—Gene Mancene
Assistant Examiner—Frank A. LaViola
Attorney, Agent, or Firm—Ware & Freidenrich

[57] ABSTRACT

A laryngoscope handle forming part of an overall laryngoscope is disclosed herein having a hollow, elongated hand gripping portion designed to contain an electrical power supply, specifically batteries, within its interior. The handle also includes a blade connecting head portion disengagably connected to one end of the hand gripping portion and a number of passageways for accommodating a light source and electrical contacts which are necessary in the operation of the overall laryngoscope. The elongated hand gripping portion itself is sealed sufficient to prevent water from reaching its interior and damaging the power supply therein. One way of forming part of this seal is a particular arrangement including a printed circuit board for sealing the entire lower end of the blade connecting head portion including its multiple passageways so as to prevent any water entering the passageways from reaching the power supply containing the interior of the hand gripping portion. The printed circuit board itself also serves as a way of electrically connecting the light source assembly and electrical contacts within the passageways in circuit with the power supply.

10 Claims, 2 Drawing Sheets

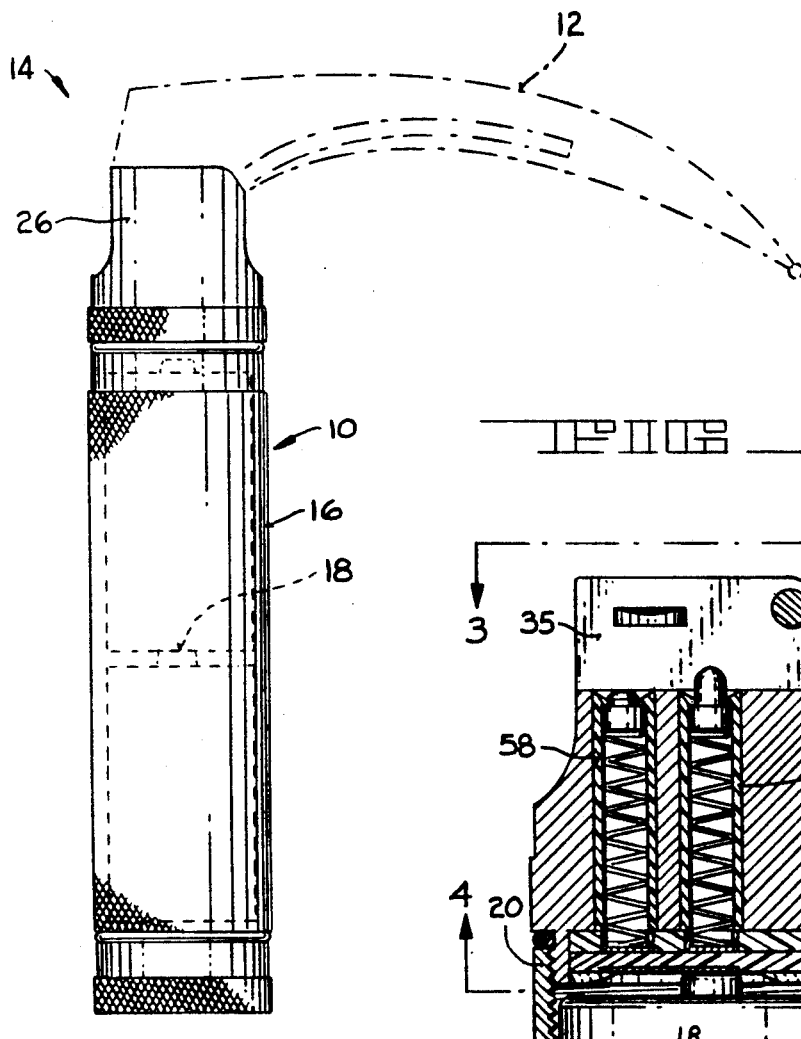
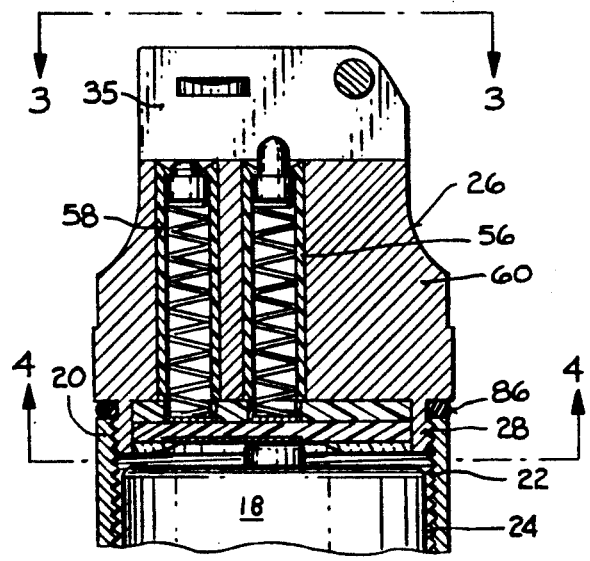
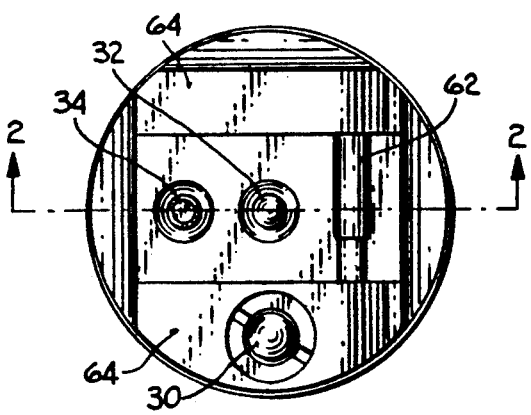
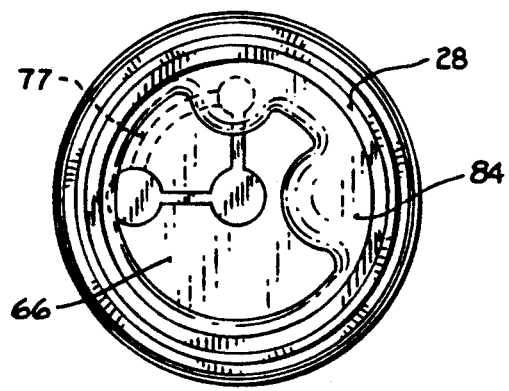

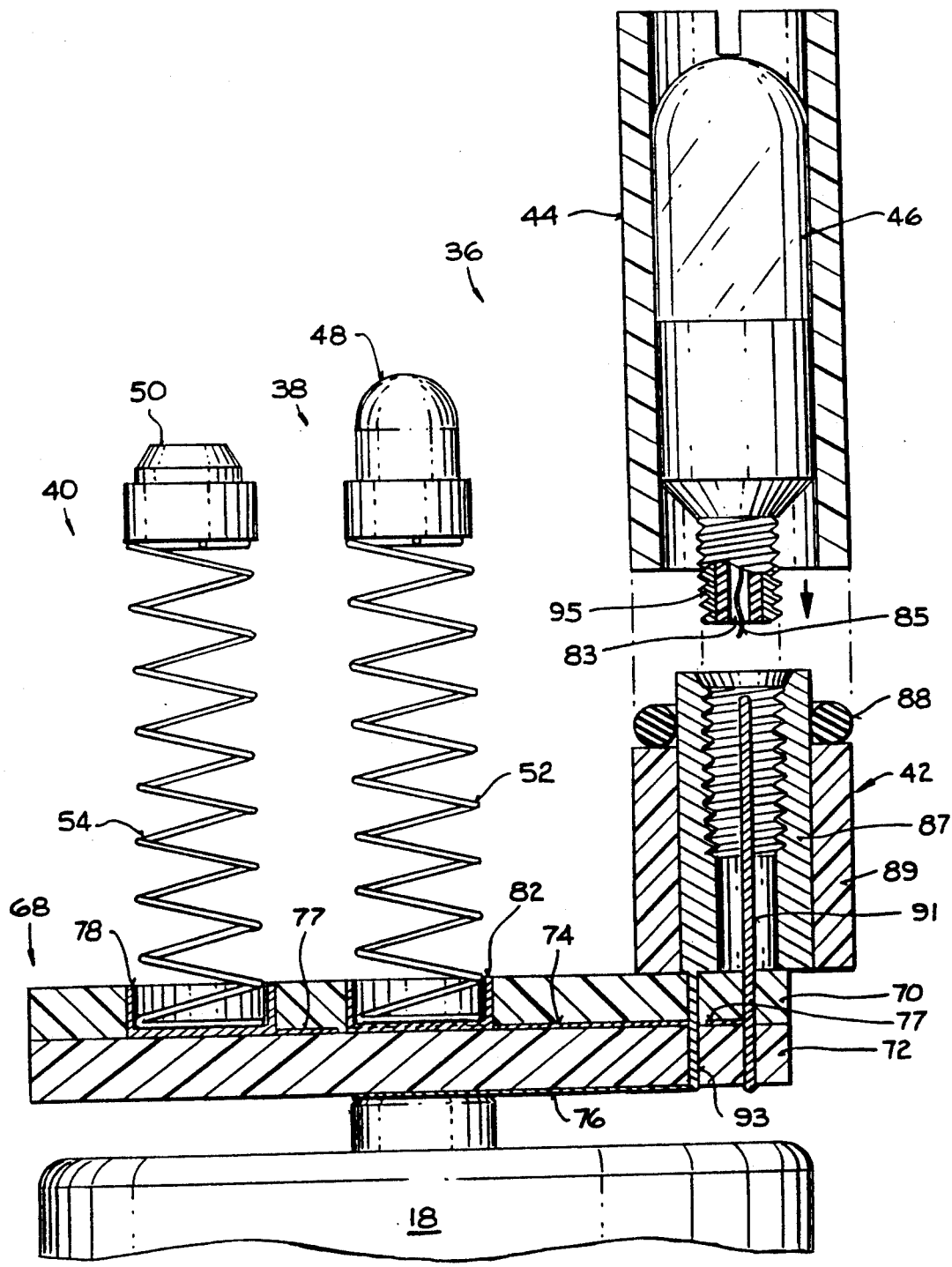
FIG_5

WATERPROOFED LARYNGOSCOPE HANDLE

FIELD OF THE INVENTION

The present invention relates generally to laryngoscopes and more particularly to a specific technique for waterproofing a laryngoscope handle so that the latter can be cleaned by submerging it in water.

BACKGROUND OF THE INVENTION

Laryngoscopes are well known in the art, as exemplified by Upsher U.S. Pat. Nos. 4,437,458; 4,406,280; and 4,517,964, all of which are incorporated herein by reference. Each of these latter patents discloses what may be referred to as a fiber optic type of laryngoscope as distinguished from the more conventional laryngoscope which does not utilize fiber optics. The conventional laryngoscope includes a handle and a blade disengagably connectable to the handle. A conventional laryngoscope blade carries its own light source which is energized by batteries contained within the handle when the blade is connected to the latter. In a fiber optics type laryngoscope, the light source is mounted on the blade engaging end of the handle and the blade includes an optical fiber which registers with and carries light from the light source when the blade is mounted to the handle so that the laryngoscope functions as if the light source were mounted on the blade.

In the case of the conventional laryngoscope, the light source carried by its blade ultimately must be placed in electrical circuit with the batteries contained within its handle. This is accomplished by providing a passageway between the interior and exterior of the handle for accommodating an electrical contact between the batteries within the handle and the blade when the latter is mounted to the handle. In the case of the fiber optics type of laryngoscope, an additional passage is required to accommodate the light source which, as stated above, is carried by handle. There is still another type of prior art laryngoscope which is compatible with both conventional and fiber optic blades, as disclosed, for example, in the previously recited Upsher U.S. Pat. Nos. 4,406,280 and 4,517,964. This combination laryngoscope includes a handle having its own light source and two contacts, one for a conventional blade and the other for a fiber optics blade. When a fiber optic blade is mounted to this handle, it engages one of the contacts in order to energize the light source carried by the handle. When a conventional blade is mounted to the handle, it engages the other contact in order to energize its own light source without energizing the light source carried by the handle. Thus the handle of this combination laryngoscope requires not one or two but three passageways through its handle.

While laryngoscope of the type described above are generally satisfactory for their intended purpose, unless their handles are waterproofed, the handles cannot be cleaned by submerging them in water because the one or more passageways for accommodating the light source and/or electrical contacts serves as leakage paths to the batteries. One of the ways to solve this problem is to waterproof the passageways individually, as described in Bauman U.S. Pat. Nos. 4,669,449; 4,679,547; 4,694,822; 4,792,367; and 4,815,451. This approach requires as many as three individually sealed passageways for some laryngoscopes. This can be complicated, expensive and not always reliable.

SUMMARY OF THE INVENTION

In view of the foregoing, it is a primary object of the present invention to waterproof a laryngoscope handle, especially one which is designed to receive both conventional and fiber optic blades, in an uncomplicated, economical and reliable manner.

A more particular object at the present invention is to waterproof the laryngoscope handle without having to seal its passageway or passageways individually.

Another particular object of the present invention is use the vary means that waterproof the laryngoscope handle for placing its light source and/or its electrical contacts in circuit with its batteries.

As will be disclosed in more detail hereinafter, the laryngoscope disclosed herein includes a handle having a hollow elongated hand gripping portion designed to contain an electrical power supply, specifically one or more batteries, within its interior and A separate and distinct blade connecting head portion. This latter component includes (1) a lower end disengagably connected to the top end of the elongated hand gripping portion, (2) an upper end designed to receive a laryngoscope blade, and (3) one or more passageways between the upper and lower ends of the head portion for accommodating a light source assembly including a light source and/or one or two contacts, depending upon whether the handle is a conventional handle, a fiber optics type handle or a combination handle, as described above.

In accordance with the present invention, this laryngoscope handle includes an arrangement for sealing the entire lower end of the blade connecting head portion including its passageway or passageways so as to prevent any water entering the passageway or passageways at the upper end of the head portion from reaching the power supply containing interior of the hand gripping portion. In that way, the individual passageways do not have to be separately sealed. The fact that water may enter these passageways when the laryngoscope handle is submerged in water is of no import. However, because the sealing arrangement designed in accordance with the present invention seals the entire lower end of the blade connecting head portion, it must also serve as a means for electrically connecting the light source assembly and/or electrical contacts contained within the passageways with the power supply so that the laryngoscope can be operated in the intended manner. In a preferred and actual working embodiment of the present invention, this sealing arrangement includes a printed circuit board extending across the entire extent of the head portions lower end for electrically connecting the light source assembly and/or the electrical contact or contacts in circuit with the power supply.

BRIEF DESCRIPTION OF THE DRAWINGS

An actual working embodiment of the present invention will be described in more detail hereinafter in conjunction with the drawing, wherein:

FIG. 1 is a side elevational view of a laryngoscope handle which is designed in accordance with the present invention and a laryngoscope blade (shown in phantom) in its operating position at the top end of the handle;

FIG. 2 is an enlarged sectional view of a top portion of the handle of FIG. 1, taken generally along line 2—2 in FIG. 3;

FIG. 3 is a top plan view of the laryngoscope handle, taken generally along line 3—3 in FIG. 2;

FIG. 4 is a bottom plan view of the portion of the laryngoscope handle illustrated in FIG. 2, taken generally along line 4—4 in FIG. 2; and FIG. 5 is a diagrammatic illustration of a sealing arrangement designed in accordance with the present invention and forming part of the top handle portion illustrated in FIG. 2 and specifically illustrating a novel light source including a light bulb shown outside its socket.

DETAILED DESCRIPTION

Turning to the drawing, wherein light components are designated by like reference numerals throughout the various figures, attention is first directed to FIG. 1. This figure depicts a laryngoscope handle 10 (in solid lines) and a laryngoscope blade 12 (in dotted lines) disengagably connected to the top end of the handle in its operating position. Handle 10 which is designed in accordance with the present invention and blade 12 together make up an overall laryngoscope generally designated by the reference numeral 14. As will be seen hereinafter laryngoscope handle 10 will be described as a combination handle, that is, one designed to a conventional blade or a fiber optics blade. However, it is to be understood that the present invention is equally applicable for use as part of a handle design strictly for conventional blades or one designed strictly for fiber optic blades.

As illustrated in FIG. 1 but shown best in FIG. 2, laryngoscope handle 10 includes a hollow, elongated hand gripping portion 16 designed to contain an electrical power supply, for example one or more batteries 18, within its interior. Elongated hand gripping portion 16 in and by itself may be conventional and, in any event, is readily providable and therefore will not be described in detail herein. It should suffice to say that its top opened end 20 is internally threaded at 22 for reasons to become apparent hereinafter. Otherwise, the hand gripping portion provides a waterproofed interior 24 for accommodating batteries 18.

Still referring to FIGS. 1 and 2, overall laryngoscope handle 10 is shown including a blade connecting head portion 26 which, as will be seen, is designed in accordance with the present invention. For the moment, it suffices to say that this head portion includes (1) an externally threaded lower end 28 which is disengagably thread connected to the threaded upper end 20 of hand gripping portion 16, (2) an upper end 30 designed in the manner to be described for disengagably receiving laryngoscope blade 12 in its operating position and (3) three passageways 30, 32, and 34 (see FIG. 3) extending between upper and lower ends of the head portion (see FIG. 2) for accommodating a light source assembly 36 and to electrical contacts 38 and 40 which are best illustrated in FIG. 5.

Light source assembly 36 includes a socket 42 for electrically and physically receiving the light bulb 44 and an insulation sleeve 46. Each of the electrical contacts 38 and 40 includes its own respective contact head 48, 50 on top of an electrically conductive spring 52, 54. The entire light source assembly 36 is disposed within passageway 30 so that light bulb 44 is visible at the too of the passageway. Contacts 38 and 40 are positioned in passageways 32 and 34, within their own insulating sleeves 56 and 58, respectively, as illustrated in FIG. 2.

For reasons to become apparent hereinafter, it is important to note that the sleeves 42, 56 and 58 serve only to electrically insulate light source assembly 36 and contacts 38 and 40 from the top portion's main body 60 which is constructed of metal or other highly electrically conductive material. There is absolutely no intent to provide nor is there provided a water seal between the exterior surfaces of the sleeves and the interior surfaces of the passageways or between the interior surfaces of the sleeves and the light source assembly or the electrical contacts. In other words, no effort is made to prevent watch from entering passageways 30, 32 and 34, either outside or within sleeves 46, 56 or 58 when handle 10 is cleaned by submerging in water. At the same time, the light source assembly and contacts must be electrically connected in circuit with batteries 18. As will be seen, this is accomplished in accordance with the present invention in a way which prevents water entering the passageways from reaching the battery containing interior 24 of hand gripping portion 16.

Before discussing the present invention in detail, attention is briefly directed to the way in which overall laryngoscope 14 functions. Assume first that laryngoscope blade 12 is a conventional blade having its own light source. It is mounted onto a top end 35 of head portion 26 in a conventional manner by means of a recessed jaw (not shown) which engages around a cross pin 62 extending across standing side walls 64, all of which form part of head portion 26. When the blade is placed in its operating position shown in FIG. 1, a contact on its underside engages contact head 48 which is shown in FIG. 2 extending up beyond its passageway 32. Note that it does not engage the contact head 50 which is recessed within its passageway 34. As a result, its circuit is completed which energizes the light source on the blade but does not energize the light bulb 44 on the handle. If blade 12 is a fiber optic type of blade, it is designed to included means for engaging contact head 50 without engaging contact head 48 so as to a circuit which energizes light bulb 44. A more detailed description of the way in which this dual bladed laryngoscope functions may be found in, for example, Upsher U.S. Pat. Nos. 4,406,280 and 4,517,964. However, it is to be understood that the present invention is not limited to the particular way in which the laryngoscope handle accommodates conventional or fiber optic blades or the particular way in which the various components are electrically interconnected to one another. Indeed, as will be seen, the present invention is equally applicable to different electrical schemes, and, for that matter, both conventional and fiber optic types of laryngoscopes.

Referring specifically to FIGS. 2, 4, and 5, attention is directed to the present invention. This invention resides in the utilization of an arrangement generally indicated at 66 in FIG. 4 for sealing the entire lower end of blade connecting head portion 26 of laryngoscope handle 10 including passageways 30, 32 and 34 so as to prevent any water entering the passageways at their upper ends from reaching the power supply containing interior 24 of hand gripping portion 16. At the same time, as will also be seen, sealing arrangement 66 includes means for electrically connecting the light source assembly 36 and electrical contacts 38 and 40 in circuit with batteries 18 in a way which allows the overall laryngoscope to operate in the manner described previously.

Specifically referring to FIG. 5, overall sealing arrangement 66 is shown including a printed circuit board 68 comprised of an upper dielectric substrate 70 laminated on top of a lower dielectric substrate 72 and a series of electrically conductive leads 74, 76 and 77. The electrically conductive leads 74 and 77 are printed on the top side of the lower substrate 72 and the electrically conductive lead 76 is printed onto the underside of substrate 72. In addition, the upper substrate 70 includes two spaced apart electrically conductive cups extending through the substrate and opening upward for receiving the contacts 40 and 38, as shown. The contacts are actually soldered into these cups so as to make a solid connection therewith. At the same time, the electrically conductive cup 78 is electrically connected to the printed lead 77 while the electrically conductive cup 82 is electrically connected to the lead 74. With particular regard to lead 77, it should be noted that, for purposes of clarity, this lead is then broken into sections at FIG. 5. It is actually a single continuous lead, as best illustrated in FIG. 4 by dotted lines.

Still referring to FIG. 5, a more detailed discussion of light source assembly 36 will now be provided. Specifically, as indicated above, this assembly includes socket 42, light bulb 44 and insulation sleeve 46. While a conventional light bulb could be provided and readily connected in circuit with the appropriate conductive leads forming part of circuit board 68, in a preferred embodiment, the light bulb and its socket are not conventional. As seen in FIG. 5, its standard contact at the bottom of the base of the light bulb has been removed so as to expose an opening 83 containing a conductive lead wire 85. At the same time, the socket is shown including an electrically conductive, internally threaded sleeve 87 contained within an insulation jacket 89 and coaxially surrounding vertically extending electrically conductive pin 91. These electrically conductive pin 91 extends through the printed circuit board and is electrically connected to the conductive lead 77. The electrically conducted sleeve 87 includes its own electrically conductive tab 93 which extends through the printed circuit board and is electrically connected to both of the conductive leads 74 and 76, thereby electrically connecting together these latter leads. When the light bulb 44 is screwed into the electrically conductive sleeve 87 of socket 42, the electrically conductive pin 91 enters the opening 83 and makes electrical contact with the electrically conductive lead 85. At the same time, the electrically conductive base 95 of the light bulb make electrical contact with sleeve 87. With the light bulb in this position, one electrical side of the light bulb (the electrically conductive wire 85) is connected in circuit with contact 40 through pin 91 and lead 77. At the same time, the other electrical side of the light bulb is connected in circuit with battery or batteries 18 and the contact 38 through tab 93 and leads 74 and 76. In order to ensure reliable electrical contact between the pin 91 and lead 77 and between the tab 93 and leads 74 and 76, these components are soldered at their joining points. This also waterproofs the area surrounding the pin 91 and tab 93.

Still referring specifically to FIG. 2, printed circuit board 66 is shown extending entirely across the otherwise opened bottom end of head portion 26 with light source assembly 36 and contacts 38 and 40 in their respective positions within sleeved passageways 30, 32 and 34. At the same time, its underside 82 faces the interior 24 of hand gripping portion 16. With the circuit board in this position, its printed lead 76 is placed in electrical contact with batteries 18. The pattern of printed leads is selected to ensure that the light source assembly 36 and contacts 38 and 40 are properly placed in circuit with batteries 18 in order to operate overall laryngoscope 14 in the intended manner.

As best illustrated in FIG. 4, with printed circuit board 68 in its operative position as described, a waterproof sealant 84, for example, silicon, is beaded around the outer periphery of the printed circuit board's underside 82 and the adjoining interior surface of the hand gripping portion so as to provide a reliable water seal. At the same time, the pin 91 and tab 93 through substrates 70 and 72 are soldered, as stated, or otherwise suitably sealed. In this way, any water entering passageways 30, 32 and/or 34 from their top ends cannot reach battery containing interior 24 of hand gripping portion 16 by these routes. However, this is accomplished without sealing the passageways individually and, at the same time, it is accomplished in an uncomplicated and reliable way while placing the light source assembly and electrical contacts in circuit with batteries 18.

In order to completely waterproof interior 24, it is only necessary to seal the joint between hand gripping portion 16 and head portion 26. Any suitable means such as O-ring 86 disposed within the joint between the two may be provided. Another seal which is important to note is illustrated in FIG. 5. Specifically, a second O-ring 88 forms part of overall light source assembly 36 and is disposed between previously described sleeve 46 and socket 42. This O-ring serves to prevent water from within or immediately outside sleeve 46 within passageway 30 from reaching the interior of socket 42.

While the present sealing technique has been described in conjunction with a particular laryngoscope including a light source assembly and two contacts, it is to be understood that the technique is equally applicable for use with other types of laryngoscopes, for example ones which include a single passageway for accommodating a single contact, as well as ones which use two passageways, one for a light source assembly and the other for a contact, as well as still other types of laryngoscopes. Moreover, the present invention is not limited to the particular printed circuit board described. The circuit board itself may include one substrate, two substrates as shown, or a multitude of substrates having the appropriate printed circuit pattern necessary to operate the laryngoscope.

What is claimed is:

1. In a laryngoscope handle having a hollow, elongated hand gripping portion designed to contain an electrical power supply within its interior and a blade connecting head portion having (i) a lower end disengagably connected to one end of said hand gripping portion, (ii) an upper end designed to receive a laryngoscope blade, and (iii) a passageway between said upper and lower ends for accommodating a light source assembly including a light source, the improvement comprising:

(a) an arrangement for sealing the entire lower end of said blade connecting head portion including said passageway so as to prevent any water entering the passageway at the upper end of the head portion from reaching the power supply containing interior of said hand gripping portion, said sealing arrangement including means for electrically connecting said light source assembly in circuit with said power supply in a way which causes the latter to energize said light source when said laryngoscope blade is mounted on said head position in a predetermined way said sealing arrangement including a printed circuit board extending across the entire extent of the head portion's lower end, said printed circuit board including at least one dielectric substrate having an underside confronting the interior of said hand gripping portion and at least one electrically conductive lead printed on said underside for electrically connecting said light source assembly in circuit with said power supply.

2. The improvement according to claim 1 wherein said sealing arrangement includes a liquid sealant extending entirely around the outer periphery of said printed circuit board between the latter and the lower end of said head portion.

3. The improvement according to claim 1 wherein said blade connecting head portion includes a second passageway between its upper and lower ends for accommodating an electrical contract, said printed circuit board including means for electrically connecting said electrical contact in circuit with said power supply.

4. The improvement according to claim 3 wherein said blade connecting head portion includes a third passageway between its upper and lower ends for accommodating a second electrical contact and wherein said printed circuit board is configured to electrically connect said second contact in circuit with said power supply.

5. The improvement according to claim 1 wherein said printed circuit board includes a second dielectric substrate laminated to the top side of said first-mentioned substrate and wherein at least one electrically conductive lead is printed on either the topside of said first-mentioned substrate or the underside of said second substrate.

6. The improvement according to claim 1 wherein said light source assembly includes a socket into which said light source is mounted, a dielectric sleeve disposed over the light source above said socket, and an O-ring seal around said light source between said jacket and said sleeve.

7. In a laryngoscope handle having a hollow, elongated hand gripping portion designed to contain an electrical power supply within its interior and a blade connecting head portion having (i) a lower end disengagably connected to one end of said hand gripping portion, (ii) an upper end designed to receive a laryngoscope blade, and (iii) a passageway between said upper and lower ends for accommodating an electrical contact, the improvement comprising:

(a) an arrangement for sealing the entire lower end of said blade connecting head portion including said passageway at the upper end of the head portion from reaching the power supply containing interior of said hand gripping portion, said sealing arrangement including means for electrically connecting said contact in circuit with said power supply, said sealing arrangement including a printed circuit board extending across the entire extent of the head portion's lower end, said printed circuit board including at least one dielectric substrate having an underside confronting the interior of said hand gripping portion and at least one electrically conductive lead point on said underside for electronically connecting said contact in circuit with said power supply.

8. The improvement according to claim 7 wherein said sealing arrangement includes a printed circuit board extending across the entire extent of the head portion's lower end for electronically connecting said contact in circuit with said power supply.

9. In a laryngoscope handle having a hollow, elongated hand gripping portion designed to contain an electrical power supply within its interior and a blade connecting head portion having (i) a lower end disengagably connected to one end of said hand gripping portion, (ii) an upper end designed to receive a laryngoscope blade, and (iii) a passageway between said upper and lower ends for accommodating a light source assembly including a light source, the improvement comprising:

(a) an arrangement for sealing the entire lower end of said blade connecting head portion including said passageway so as to prevent any water entering the passageway at the upper end of the head portion from reaching the power supply containing interior of said hand gripping portion, said sealing arrangement including means for electrically connecting said light source assembly in circuit with said power supply in a way which causes the latter to energize said light source when said laryngoscope blade is mounted on said head position in a predetermined way, said blade connecting head portion including a second passageway between its upper and lower ends for accommodating an electrical contact, said sealing arrangement including means for electrically connecting said electrical contact in circuit with said power supply, said sealing arrangement including a printed circuit board extending across the entire extent of head portion's lower end for electrically connecting said light source and said contact in circuit with said power supply, said blade connecting head portion including a third passageway between its upper and lower ends for accommodating a second electrical contact and where said printed circuit board is configured to electrically connect said second contact in circuit with said power supply, said printed circuit board including at least one dielectric substrate having an underside confronting the interior of said hand gripping portion and at least one electrically conductive lead printed on said underside.

10. The improvement according to claim 9 wherein said printed circuit board includes a second dielectric substrate laminated to the top side of said first-mentioned substrate and wherein at least one electrically conductive lead is printed on either the topside of said first-mentioned substrate or the underside of said second substrate.

* * * * *